United States Patent
Li

(10) Patent No.: US 11,350,836 B2
(45) Date of Patent: Jun. 7, 2022

(54) CURRENT CANCELLATION CIRCUIT, HEART RATE DETECTION DEVICE AND WEARABLE DEVICE

(71) Applicant: SHENZHEN GOODIX TECHNOLOGY CO., LTD., Shenzhen (CN)

(72) Inventor: Bo Li, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/023,529

(22) Filed: Sep. 17, 2020

(65) Prior Publication Data
US 2021/0000357 A1    Jan. 7, 2021

Related U.S. Application Data

(63) Continuation of application No. PCT/CN2019/074287, filed on Jan. 31, 2019.

(51) Int. Cl.
*A61B 5/024* (2006.01)
*A61B 5/00* (2006.01)
*H03M 1/46* (2006.01)

(52) U.S. Cl.
CPC ...... *A61B 5/02427* (2013.01); *A61B 5/02438* (2013.01); *A61B 5/681* (2013.01); *A61B 5/6803* (2013.01); *H03M 1/462* (2013.01)

(58) Field of Classification Search
None
See application file for complete search history.

(56) References Cited

U.S. PATENT DOCUMENTS

| | | | |
|---|---|---|---|
| 5,008,672 A | 4/1991 | Leedy | |
| 8,368,577 B2 | 2/2013 | Aruga et al. | |
| 9,634,682 B1 | 4/2017 | Fsai et al. | |
| 10,349,848 B2 | 7/2019 | Pi et al. | |

(Continued)

FOREIGN PATENT DOCUMENTS

| | | |
|---|---|---|
| CN | 102204107 A | 9/2011 |
| CN | 106725323 A | 5/2017 |

(Continued)

*Primary Examiner* — Katherine L Fernandez

(57) ABSTRACT

A current cancellation circuit, a heart rate detection device and a wearable device. The current cancellation circuit includes: a current-voltage conversion circuit and a SAR ADC, where the SAR ADC includes a DAC, an SAR logic circuit and a comparator; the current-voltage conversion circuit is configured to receive an analog current output by the DAC and an interference current output by a photoelectric sensor, calculate a difference between the analog current and the interference current, and output an analog voltage; the comparator is configured to receive the analog voltage output by the current-voltage conversion circuit, and output a comparison result according to the analog voltage; and the DAC is configured to output the analog current according to a digital signal corresponding to the comparison result that is output by the SAR logic circuit, and the analog current is used to cancel the interference current output by the photoelectric sensor.

19 Claims, 3 Drawing Sheets

(56) References Cited

U.S. PATENT DOCUMENTS

| | | | | |
|---|---|---|---|---|
| 2009/0251344 A1* | 10/2009 | Wong | ............... | H03M 1/002 |
| | | | | 341/122 |
| 2011/0205099 A1 | 8/2011 | Inoue | | |
| 2011/0234433 A1 | 9/2011 | Aruga et al. | | |
| 2016/0373124 A1* | 12/2016 | Kijima | ............... | H03M 1/38 |
| 2017/0360315 A1 | 12/2017 | Pi et al. | | |
| 2018/0156660 A1* | 6/2018 | Turgeon | ............... | G01J 1/46 |
| 2020/0163562 A1* | 5/2020 | Neaves | ............... | A61B 5/681 |

FOREIGN PATENT DOCUMENTS

| | | |
|---|---|---|
| CN | 106788276 A | 5/2017 |
| CN | 107980208 A | 5/2018 |
| CN | 108141219 A | 6/2018 |
| EP | 0376554 A2 | 7/1990 |

* cited by examiner

CURRENT CANCELLATION CIRCUIT, HEART RATE DETECTION DEVICE AND WEARABLE DEVICE

CROSS REFERENCE TO RELATED APPLICATIONS

The present application is a continuation of international application No. PCT/CN2019/074287, filed on Jan. 31, 2019, which is hereby incorporated by reference in its entirety.

TECHNICAL FIELD

Embodiments of the present application relate to the field of electronic technologies, and more particularly, to a current cancellation circuit, a heart rate detection device and a wearable device.

BACKGROUND

Photoplethysmograph (PPG) technology is a technology for human exercise heart rate detection. Specifically, a photoelectric sensor may be configured to detect an intensity of reflected light after absorption by human blood and tissues, then, trace a change in blood vessel volume during a cardiac cycle, and a human heart rate was calculated according to the traced pulse waveform.

In PPG detection, if there is too much background light, a channel of a PPD detection circuit is saturated, and then the detection fails. In related technologies, an additional background light cancellation (BGC) circuit is configured to cancel the background light to ensure the normal operation of the channel. However, the use of BGC will increase noise of the channel, and the use of the BGC circuit requires participation of an external algorithm circuit to cancel the background light, which increases complexity and cost of the detection circuit.

SUMMARY

Embodiments of the present application provide a current cancellation circuit, a heart rate detection device and a wearable device, which could reduce complexity and cost of a PPG detection circuit.

A current-voltage conversion circuit and a successive approximation SAR analog-to-digital converter ADC, where the SAR ADC includes a digital-to-analog converter DAC, an SAR logic circuit and a comparator;

the current-voltage conversion circuit is configured to receive an analog current output by the DAC and an interference current output by a photoelectric sensor, calculate a difference between the analog current and the interference current, and output an analog voltage, where the interference current is obtained by photoelectric conversion of an interference light signal by the photoelectric sensor;

the comparator is configured to receive the analog voltage output by the current-voltage conversion circuit, and output a comparison result according to the analog voltage; and the DAC is configured to output the analog current according to a digital signal corresponding to the comparison result that is output by the SAR logic circuit, and the analog current is used to cancel the interference current output by the photoelectric sensor.

In some possible implementation manners, the SAR logic circuit is particularly configured to:

determine the digital signal, and control, according to the digital signal, the DAC to output a next analog current so that the next analog current is more approximate to the interference current.

In some possible implementation manners, the SAR logic circuit determines the digital signal according to a dichotomy.

In some possible implementation manners, the DAC is particularly configured to:

output, according to a current analog current and the digital signal, a next analog current, and input the next analog current to the current-voltage conversion circuit.

In some possible implementation manners, the DAC is a resistive DAC, the resistive DAC includes N first resistors, the current cancellation circuit further includes N first switches, and the N first resistors are in one-to-one correspondence to the N first switches, where N is a number of bits of the digital signal output by the SAR ADC; and the SAR logic circuit is further configured to:

control, according to the digital signal, a corresponding first switch so that a first resistor corresponding to the first switch is connected to a first voltage or a second voltage.

In some possible implementation manners, the SAR logic circuit is particularly configured to:

control, if the digital signal is 1, the first switch so that the first resistor corresponding to the first switch is connected to the first voltage; or control, if the digital signal is 0, the first switch so that the first resistor corresponding to the first switch is connected to the second voltage.

In some possible implementation manners, the DAC is a single-ended resistive DAC, and the current-voltage conversion circuit is a transimpedance amplifier TIA, where the TIA includes a first input end, a common mode input end, a first output end and a second output end, an output end of the single-ended resistive DAC is connected to the first input end of the TIA, an output end of the photoelectric sensor is also connected to the first input end of the TIA, the common mode input end of the TIA is configured to input a common mode voltage, the first output end of the TIA is connected to a first input end of the comparator, the second output end of the TIA is connected to a second input end of the comparator, an output end of the comparator is connected to an input end of the SAR logic circuit, and an output end of the SAR logic circuit is connected to an input end of the single-ended resistive DAC.

In some possible implementation manners, the DAC is a differential resistive DAC, the differential resistive DAC further includes N second resistors, the current cancellation circuit further includes N second switches, the N second resistors are in one-to-one correspondence to the N second switches, and the SAR logic circuit is further configured to:

control, according to an inverted signal of the digital signal, a corresponding second switch so that a second resistor corresponding to the second switch is connected to the second voltage or the first voltage.

In some possible implementation manners, the SAR logic circuit is particularly configured to:

control, if the digital signal is 1, the second switch so that the second resistor corresponding to the second switch is connected to the second voltage; or control, if the digital signal is 0, the second switch so that the second resistor corresponding to the second switch is connected to the first voltage.

In some possible implementation manners, the current-voltage conversion circuit is a differential TIA, the differential TIA includes a first input end, a second input end, a common mode input end, a first output end and a second output end, a first output end and a second output end of the differential resistive DAC are respectively connected to the first input end and the second input end of the differential TIA, a first end and a second end of the photoelectric sensor are respectively connected to the first input end and the second input end of the differential TIA, the common mode input end of the differential TIA is configured to input a common mode voltage, the first output end and the second output end of the differential TIA are respectively connected to a first input end and a second input end of the comparator, an output end of the comparator is connected to an input end of the SAR logic circuit, and an output end of the SAR logic circuit is connected to an input end of the differential resistive DAC.

In some possible implementation manners, the first voltage is a reference voltage, and the second voltage is a ground voltage or a common mode voltage.

In some possible implementation manners, an output end of the DAC is connected to an input end of the current-voltage conversion circuit, the input end of the current-voltage conversion circuit is simultaneously connected to an output end of the photoelectric sensor, output ends of the current-voltage conversion circuit is connected to input ends of the comparator, an output end of the comparator is connected to an input end of the SAR logic circuit, and an output end of the SAR logic circuit is connected to an input end of the DAC.

In some possible implementation manners, the photoelectric sensor is a photodiode.

In a second aspect, a heart rate detection device is provided, including:

the current cancellation circuit in the first aspect or any one of possible implementation manners of the first aspect.

In some possible implementation manners, the heart rate detection device further includes:

a transmitting circuit configured to transmit a light signal for heart rate detection; and a receiving circuit including a photoelectric sensor and an analog-to-digital converter ADC;

where the photoelectric sensor is connected to an input end of a current-voltage conversion circuit in the current cancellation circuit, and configured to receive the light signal, and perform photoelectric conversion on the received light signal to obtain a current signal; the current signal is input to the input end of the current-voltage conversion circuit; and the ADC is connected to an output end of the current-voltage conversion circuit, and configured to receive an analog voltage output by the current-voltage conversion circuit.

In some possible implementation manners, in a first stage, the transmitting circuit does not transmit a light signal, the photoelectric sensor receives an interference light signal and performs photoelectric conversion on the interference light signal to obtain an interference current, the current cancellation circuit determines a digital signal output by a successive approximation SAR analog-to-digital converter ADC in the current cancellation circuit according to the interference current and controls a digital-to-analog converter DAC in the current cancellation circuit to output a corresponding analog current according to the digital signal, and the analog current is used to cancel the interference current; and in a second stage, the transmitting circuit transmits a light signal for heart rate detection, the photoelectric sensor receives the interference light signal and the light signal for heart rate monitoring, and performs photoelectric conversion on the interference light signal and the light signal for heart rate monitoring to obtain a mixed current, where the mixed current includes the interference current and a signal current generated from the light signal for heart rate monitoring, the DAC outputs the analog current, and the current-voltage conversion circuit receives the mixed current and the analog current, calculates a difference between the mixed current and the analog current, and outputs the analog voltage to the ADC.

In a third aspect, a wearable device is provided, the heart rate detection device in the second aspect or any one of possible implementation manners of the second aspect.

Based on the foregoing technical solutions, a current cancellation circuit of the embodiments of the present application controls an analog current output by a DAC through SAR logic inside an SAR ADC so that the analog current is successively approximate to an interference current to be cancelled out without participation of an additional algorithm circuit, which is beneficial for simplifying a circuit structure and reducing circuit cost.

DESCRIPTION OF EMBODIMENTS

Technical solutions of embodiments of the present application will be described below, in combination with the accompanying drawings in the embodiments of the present application.

Figure 1:
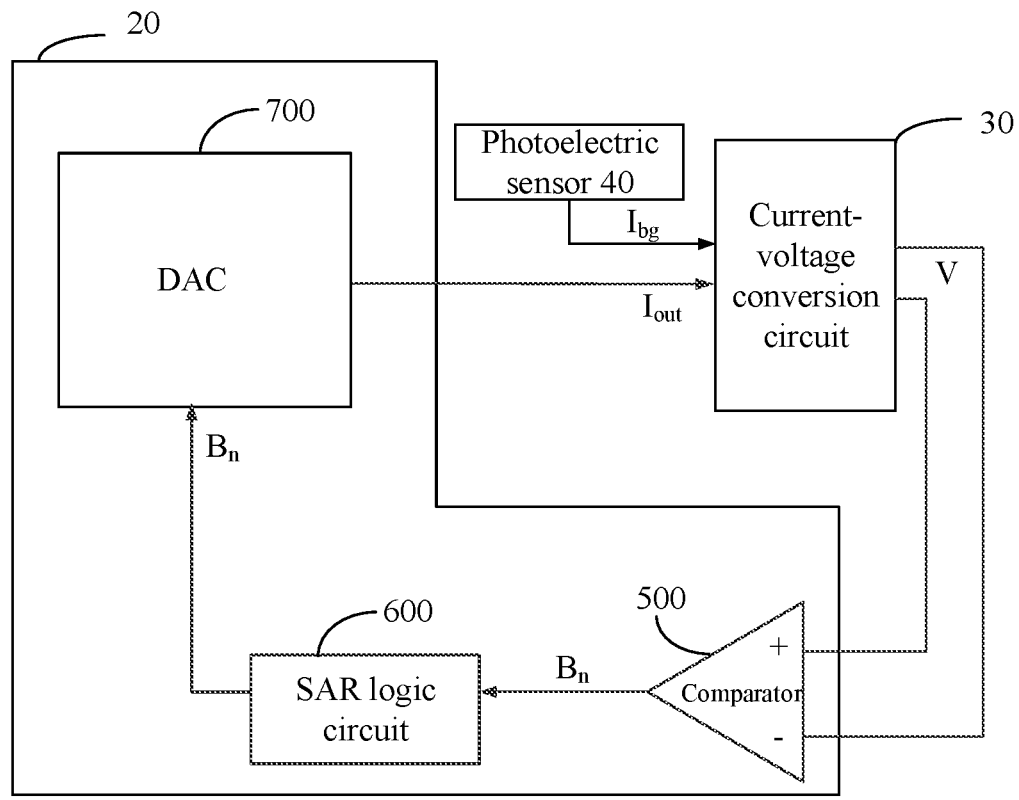
FIG. 1 is a schematic structural block diagram of a current cancellation circuit provided according to an embodiment of the present application.

FIG. 1 is a schematic structural block diagram of a current cancellation circuit according to an embodiment of the present application.

As shown in FIG. 1, a current cancellation circuit 10 may be configured to cancel an interference current $I_{bg}$ obtained by photoelectric conversion of an interference light signal by a photoelectric sensor 40. Specifically, the current cancellation circuit 10 may include: a successive approximation analog-to-digital converter (SAR ADC) 20 and a current-voltage conversion circuit 30, and the SAR ADC 20 may include a DAC 700, an SAR logic circuit 600 and a comparator 500.

In one implementation manner, an output end of the DAC 700 is connected to an input end of the current-voltage conversion circuit 30, an output end of the photoelectric sensor 40 is connected to an input end of the current-voltage conversion circuit 30, output ends of the current-voltage conversion circuit 30 are connected to input ends of the comparator, an output end of the comparator 500 is connected to an input end of the SAR logic circuit 600, and an output end of the SAR logic circuit 600 is connected to an input end of the DAC 700.

Optionally, in some embodiments, the photoelectric sensor 40 may be a photodiode or another photoelectric conversion device, which is not limited in the embodiment of the present application.

Optionally, in some embodiments, the interference light signal may be a background light signal. For example, the photoelectric sensor 40 may perform photoelectric conversion on the background light signal that affects heart rate detection to obtain the interference current, and the interference current is a current to be cancelled out. That is, the current cancellation circuit of the embodiment of the present application may be applied to background light cancellation in heart rate monitoring. Certainly, the current cancellation circuit of the embodiment of the present application may also be applicable to other scenarios where interference light signal cancellation is required. For example, in fingerprint detection, the current cancellation circuit may be configured to eliminate the effect of a background light signal that affects the fingerprint detection on the fingerprint detection, which is not limited in the embodiment of the present application.

Specifically, the SAR ADC 20 is configured to convert an analog signal into a digital signal, for example, to convert an analog current or analog voltage into an N-bit binary code. In some embodiments, the SAR logic circuit 600 in the SAR ADC 20 is configured to sequentially output each bit of the N-bit binary code based on control of a clock signal, and the DAC 700 is configured to output a corresponding analog signal, for example, an analog current or analog voltage, according to each bit output by the SAR logic circuit 600. In the embodiment of the present application, in order to cancel the interference current generated from the interference light signal, the DAC 700 may adopt a current output type DAC, for example, a resistive DAC, that is, the DAC 700 may convert a digital signal into an analog current.

Further, the DAC 700 inputs the output analog current to the current-voltage conversion circuit 30, and then the current-voltage conversion circuit 30 may output an analog voltage according to the analog current and the interference light current $I_{bg}$ output from the photoelectric sensor 40. For example, a difference between the analog current and the interference current $I_{bg}$ may be calculated, and the analog voltage is output.

In the embodiment of the present application, the SAR logic circuit 600 may control the analog current output by the DAC 700 by controlling the output N-bit binary code. It can be understood that when the analog current is gradually close to the interference current, the analog voltage output by the current-voltage conversion 30 gradually decreases, and when the SAR ADC determines each bit of the N-bit binary code, the analog current output by the DAC 700 becomes stable. In this case, the analog current is equal to or closest to the interference current, and the analog voltage output by the current-voltage conversion circuit 30 is zero or close to zero.

Optionally, in the embodiment of the present application, the current-voltage conversion circuit 30 may be a transimpedance amplifier (TIA), or may be another circuit capable of converting a current signal into a voltage signal, which is not limited in the embodiment of the present application. The following will be explained mainly by an example that the current-voltage conversion circuit is a TIA, which should not constitute any limitation to the present application.

It should be understood that in practical applications, the existing PPG detection circuit usually includes a TIA. In the embodiment of the present application, in order to realize automatic interference light cancellation, the TIA in the PPG detection circuit may be reused, a resistance type DAC, a comparator and an SAR logic circuit are further added, and the foregoing added circuits would not increase channel noise and area overheads too much. Moreover, the analog current output by the DAC is controlled by the SAR logic circuit in the SAR ADC to be successively approximate to the interference current, so as to achieve the purpose of cancelling the interference current without participation of an additional algorithm circuit, which is beneficial for meeting the overall needs for performance and cost of a system.

Optionally, in one embodiment of the present application, the SAR logic circuit may first determine the most significant bit (MSB) of the N-bit binary code, referred to as the highest bit for short, and then sequentially determine each of the other bits of the N-bit binary code.

Specifically, in order to determine the MSB, the DAC 700 inputs the first analog current to the current-voltage conversion circuit 30, and the current-voltage conversion circuit 30 may calculate a difference between the first analog current and the interference current and determine the first analog voltage. Further, the comparator 500 outputs the first comparison result according to the first analog voltage, and outputs the first comparison result to the SAR logic circuit 600, where the first comparison result corresponds to the MSB. Then, the SAR logic circuit 600 determines the MSB according to the first comparison result output by the comparator 500, and controls the DAC to output a next analog current according to the MSB.

Then, the current-voltage conversion circuit 30 may calculate a difference between the next analog current and the interference current and determine a next analog voltage. The comparator 500 may output a next comparison result according to the next analog voltage, and the next comparison result corresponds to a next bit of the N-bit binary code, that is, a second most significant bit. The process is repeated in this way, and each bit of the N-bit binary code is obtained.

Optionally, in one embodiment of the present application, the magnitude of the analog voltage output by the current-voltage conversion circuit 30 may be used to determine a next bit of the N-bit binary code input to the DAC 700.

It can be understood that the magnitude of the analog voltage output by the current-voltage conversion circuit 30 reflects a magnitude relationship between the analog current output by the DAC and the interference current. Therefore, the next bit of the N-bit binary code may be determined according to a magnitude relationship between the current analog current and the interference current so that a next analog current is more approximate to the interference current.

For example, if the analog voltage is greater than zero, this case can be considered that the analog current output by the DAC 700 is less than the interference current, the analog current output by the DAC 700 needs to be increased, thus, the comparator may output a comparison result of 1, and further, the SAR logic circuit 600 may determine that a next bit of the N-bit binary code is 1 so that a next analog current is greater than the interference current; or if the analog voltage is less than zero, it can be considered that the analog current output by the DAC 700 is greater than the interference current, the analog current output by the DAC 700 needs to be decreased, the comparator may output a comparison result of 0, and further, the SAR logic circuit 600 may determine that a next bit of the N-bit binary code is 0 so that a next analog current is less than the interference current.

It can be understood that the SAR logic circuit 600 may include a circuit configured to implement any one of a number of SAR calculations. For example, the SAR logic circuit 600 may be configured as a circuit that implements a dichotomous SAR calculation, or the SAR logic circuit 600 may be configured as a circuit that implements a linear SAR calculation, which is not limited in the embodiment of the present application. In some embodiments, the SAR logic circuit 600 may be designed and constituted using processes known to those skilled in the art. A specific implementation of the SAR logic circuit will be explained below by an example of a dichotomy, which should not constitute any limitation to the present application.

Optionally, in the embodiment of the present application, the DAC 700 may be configured to implement any circuit that converts a digital signal into an analog current. For example, the DAC 700 may be configured as a resistive DAC or a resistive-capacitive DAC, which is not limited in the embodiment of the present application. The following will be explained by an example that the DAC 700 adopts a resistive DAC, which should not constitute any limitation to the present application.

Figure 2:
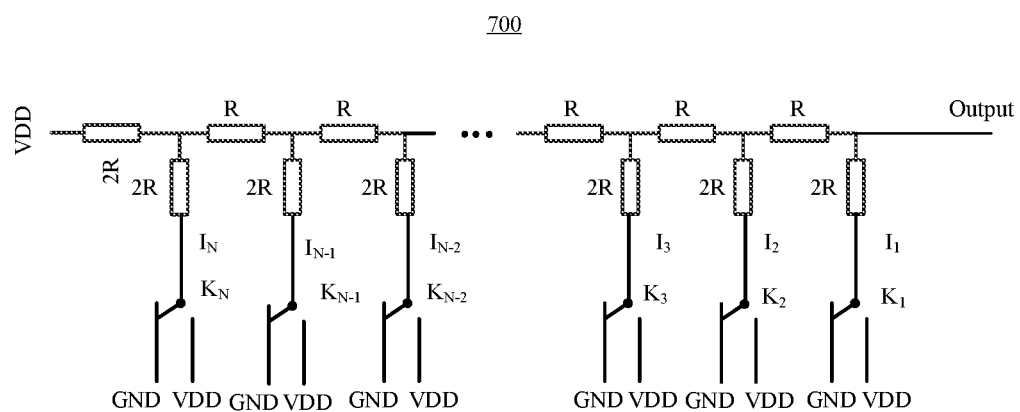
FIG. 2 is a schematic structural diagram of a DAC implemented with a single-ended resistive DAC.

FIG. 2 is a schematic structural diagram of the DAC 700 implemented with a single-ended resistive DAC. As shown in FIG. 2, the DAC 700 may include a resistor array (including N+1 resistors 2R and N−1 resistors R) and a switch array $K_1 \sim K_N$, and N resistors (resistors 2R) in the resistor array are respectively connected to a ground voltage GND or a reference voltage VDD through one of N switches. The SAR logic circuit 600 may control a corresponding switch of the N switches to be connected to a first voltage or a second voltage according to the N-bit binary code. The following will be explained by an example that the first voltage is the reference voltage VDD and the second voltage is the ground voltage GND.

For example, the SAR logic circuit 600 may control the corresponding switch to be connected to the reference voltage when a bit of the N-bit binary code is 1, or control the corresponding switch to be connected to the ground voltage GND when a bit of the N-bit binary code is 0, where the lowest bit of the N-bit binary code is used to control the leftmost switch $K_N$, and the highest bit of the N-bit binary code is used to control the rightmost switch $K_1$.

In the circuit structure shown in FIG. 2, from the perspective of any node to left, an equivalent resistance is 2R, and when each switch is turned on individually, currents that the DAC can output are:

$$I_1 = \frac{VDD}{2R}, I_2 = \frac{1}{2}I_1, I_3 = \frac{1}{4}I_1, \ldots, I_{N-2} = \frac{1}{2^{(N-3)}}I_1,$$
$$I_{N-1} = \frac{1}{2^{(N-2)}}I_1, I_N = \frac{1}{2^{(N-1)}}I_1;$$

where VDD/R is a reference current, that is, a maximum current that the DAC 700 can output. Therefore, after the N-bit binary code output by the SAR logic circuit 600 is converted by the DAC, analog currents proportional to the N-bit binary code may be obtained. That is, the SAR logic circuit 600 controls different outputs of the N-bit binary code, and $2^N$ analog currents may be obtained. In this way, the SAR logic circuit 600 may determine an N-bit binary code corresponding to an analog current with the smallest error from the interference current by successive approximation logic, that is, the N-bit binary code output by the SAR ADC.

Figure 3:
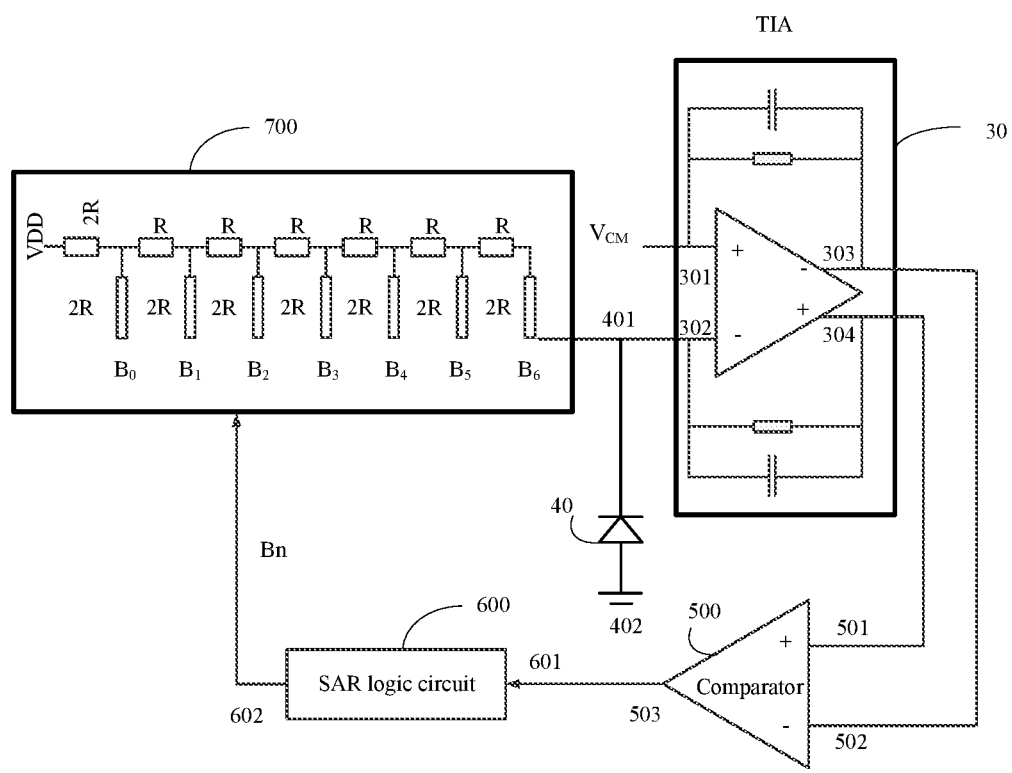
FIG. 3 is a schematic structural diagram of a current cancellation circuit implemented with a single-ended resistive DAC.

FIG. 3 is a schematic structural diagram of the current cancellation circuit when the DAC adopts the single-ended resistive DAC shown in FIG. 2. Specific working principles will be explained in combination with FIG. 2 and FIG. 3. It should be understood that FIG. 3 is explained by an example of a 7-bit DAC. Certainly, the DAC may have other digits, such as 8 bits, or 12 bits.

Specifically, the TIA may include a first input end 302, a common mode input end 301, a first output end 303 and a second output end 304, an output end of the DAC 700 is connected to the first input end 302 (such as an inverting input end) of the TIA, the second input end 301 of the TIA 30 is configured to input a common mode voltage, one end 401 of the photoelectric sensor 40 is also connected to the first input end 302 of the TIA, the other end 402 of the photoelectric sensor 40 is grounded, the first output end 303 of the TIA 30 is connected to a first input end 502 of the comparator 500, the second output end 304 of the TIA 30 is connected to a second input end 501 of the comparator 500, an output end 503 of the comparator is connected to an input end 601 of the SAR logic circuit 600, and an output end 602 of the SAR logic circuit 600 is connected to an input end of the DAC 700.

In a specific implementation, the SAR logic circuit 600 may first determine the highest bit of the N-bit binary code. Specifically, in a first period of time, a switch $K_1$ is connected to VDD, and the other switches are connected to GND. In this case, the analog current output by the DAC is $I_1$, and the analog current $I_1$ and the interference current $I_{bg}$ are input to the TIA 30. The TIA 30 calculates a difference between the analog current $I_1$ and the interference $I_{bg}$, and outputs an analog voltage V 1. The comparator 500 receives the analog voltage $V_1$, determines a comparison result according to the analog voltage $V_1$, and then feeds back the comparison result to the SAR logic circuit 600 so that the SAR logic circuit 600 may adjust the analog current output by the DAC according to the comparison result. For example, if the comparison result is 1, the SAR logic circuit 600 considers that the interference current is greater than the analog current $I_1$, and the output analog current needs to be increased, so as to determine that the highest bit is 1, and control the corresponding switch $K_1$ to be connected to VDD to retain the analog current $I_1$; or if the comparison result is 0, the SAR logic circuit 600 considers that the interference current is less than the analog current $I_1$, and the output analog current needs to be decreased, so as to determine that the highest bit is 0, and control the switch $K_1$ to be connected to GND to purge the analog current $I_1$.

Then, in a second time period, a switch $K_2$ is controlled to be connected to VDD, and switches $K_3 \sim K_N$ are controlled to be connected to GND. In this case, the analog current output by the DAC is $I_1+I_2$, and the analog current $I_1+I_2$ and the interference current $I_{bg}$ are input to the TIA 30. The TIA 30 calculates a difference between the analog current $I_1+I_2$ and the interference $I_{bg}$, and outputs an analog voltage $V_2$. Further, the comparator 500 determines a next comparison result according to the analog voltage $V_2$, and then feeds back the next comparison result to the SAR logic circuit 600 so that the SAR logic circuit 600 may adjust the analog current output by the DAC according to the comparison result. For example, if the comparison result is 1, the SAR logic circuit 600 determines that the interference current is greater than the analog current $I_1+I_2$, and the analog current output by the DAC needs to be increased, so as to determine that the second most significant bit is 1, and control the switch $K_2$ to be connected to VDD to retain an analog current $I_2$; or if the comparison result is 0, the SAR logic circuit 600 determines that the interference current is less than the analog current $I_1+I_2$, and the analog current output by the DAC needs to be decreased, so as to determine that the second most significant bit is 0, and control the switch $K_2$ to be connected to GND to purge the analog current $I_2$.

The foregoing process is performed cyclically until each bit of the N-bit binary code is determined. In this case, the analog current output by the DAC 700 is closest to the interference current. Therefore, the embodiment of the present application could achieve the purpose of cancelling the interference current through the SAR logic circuit inside the SAR ADC without participation of an additional algorithm circuit, which is beneficial for simplifying the circuit structure.

It should be understood that in the embodiment shown in FIG. 3, the successive approximation is started only with an initial state of 1000000, and in other alternative embodiments, the successive approximation may be started with other states. For example, the successive approximation is started with an initial state of 0111111, and in this way, only the logic implementation of the SAR logic circuit needs to be adjusted. That is, in the initial state, the N switches may be connected to any voltage. The specific principles are similar, which will not be repeated redundantly herein. The specific working principles when the DAC is implemented with a single-ended resistive DAC have been introduced above in combination with FIG. 2 and FIG. 3. Specific working principles when the DAC is implemented with a differential resistive DAC will be introduced below in combination with FIG. 4. It should be understood that the working principles of the single-ended resistive DAC and the differential resistive DAC are similar. Reference is made to the foregoing embodiments for the similar description, which will not be repeated redundantly herein.

Figure 4:
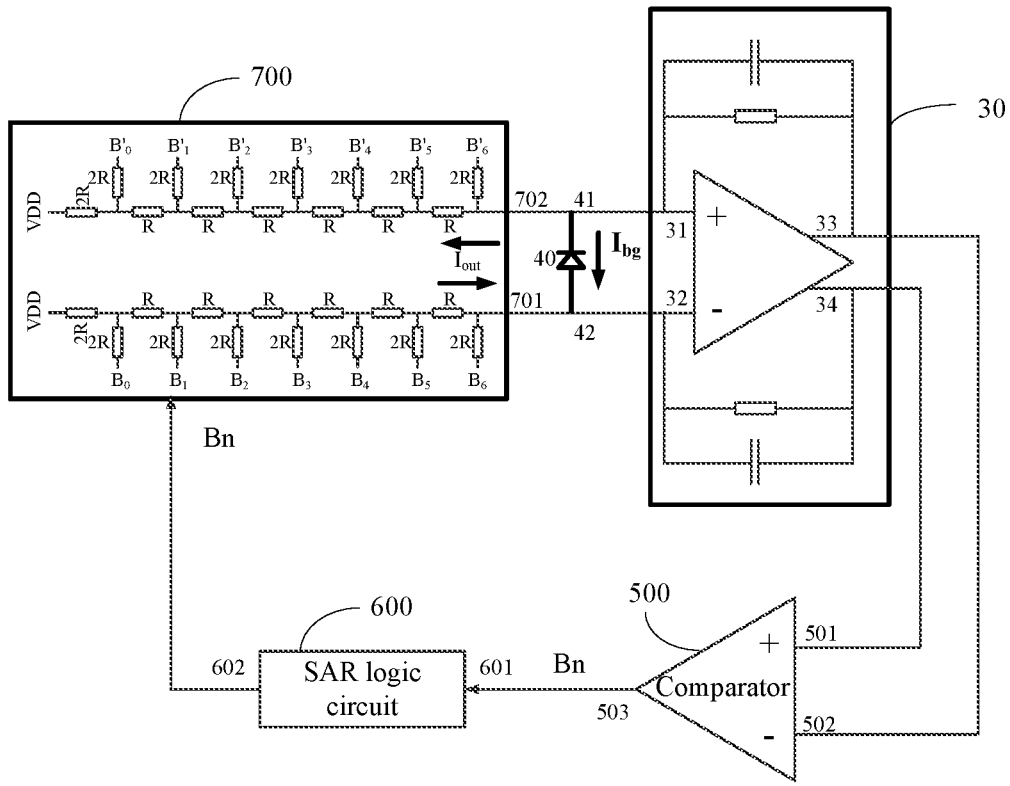
FIG. 4 is a schematic structural diagram of a current cancellation circuit implemented with a differential resistive DAC.

FIG. 4 illustrates a schematic structural diagram of a current cancellation circuit implemented with a DAC adopting a differential resistive DAC. As shown in FIG. 4, the DAC 700 may include two symmetrical resistor arrays, a first resistor array and a second resistor array. An output end 701 of the first resistor array and an output end 702 of the second resistor array are output ends of the DAC 700. Correspondingly, the TIA 30 is a differential TIA having a first input end 31 (that is, a non-inverting input end), a second input end 32 (that is, an inverting input end) and a common mode input end (not shown), a first output end 33 and a second output end 34.

Specifically, the output end 701 of the first resistor array and the output end 702 of the second resistor array are respectively connected to the first input end 31 and the second input end 32 of the differential TIA 30, while a first end 41 and a second end 42 of the photoelectric sensor 40 are also respectively connected to the first input end 31 and the second input end 32 of the differential TIA 30, the common mode input end of the differential TIA 30 is configured to input a common mode voltage, the first output end 33 and the second output end 34 of the differential TIA 30 are respectively connected to a first input end 502 and a second input end 501 of the comparator 500, an output end 503 of the comparator 500 is connected to an input end 601 of the SAR logic circuit 600, and an output end 602 of the SAR logic circuit 600 is connected to the DAC 700.

In this embodiment, the first resistor array includes N first resistors, denoted as $R_{11}$~$R_{1N}$, the N first resistors are connected to N first switches, denoted as $K_{11}$~$K_{1N}$, and each first switch is configured to control a corresponding first resistor to be connected to a first voltage or a second voltage. Symmetrically, the second resistor array includes N second resistors, denoted as $R_{21}$~$R_{2N}$, the N second resistors are connected to N second switches, denoted as $K_{21}$~$K_{2N}$, and each second switch is configured to control a corresponding second resistor to be connected to the first voltage or the second voltage.

It should be understood that in this embodiment, control signals of the first switches and the corresponding second switches are opposite. That is, when a first switch $K_{1n}$ is connected to the first voltage, a corresponding second switch $K_{2n}$ is connected to the second voltage. That is, when a first resistor $R_{1n}$ is connected to the first voltage, a corresponding second resistor Ren is connected to the second voltage.

The control signals of the N first switches are an N-bit binary code determined by the SAR logic circuit 600, and the control signals of the N second switches is inverted signals of the N-bit binary code. Specifically, the n-th bit $B_n$ of the N-bit binary code is used to control the switch $K_{1n}$, and an inverted signal $B'_n$ of $B_n$ is used to control the switch $K_{1n}$.

In one control mode, when $B_n$ is 1, $K_{1n}$ is controlled to be connected to the first voltage, and $K_{2n}$ is controlled to be connected to the second voltage; or when $B_n$ is 0, $K_{1n}$ is controlled to be connected to the second voltage, and Ken is controlled to be connected to the first voltage.

Optionally, in the embodiment of the present application, the first voltage is VDD, the second voltage is a ground voltage GND or a common mode voltage, or another voltage. The following will be explained by an example that the first voltage is VDD and the second voltage is a ground voltage.

Working principles of the current cancellation circuit will be explained in detail below in combination with FIG. 4.

In a first stage, the N first resistors in the first resistor array and the N second resistors in the second resistor array of the DAC 700 are all grounded, and an analog current $I_0$ output by the DAC is 0. In this case, an analog voltage $V_0$ output by the differential TIA 30 is generated from the interference current $I_{bg}$. Then, the differential TIA 30 outputs the analog voltage $V_0$ to the first input end 501 and the second input end 502 of the comparator 500, and the comparator 500 determines a comparison result according to the magnitudes of the voltages input from the first input end 501 and the second input end 502.

In one implementation manner, if the analog voltage $V_0$ is greater than zero, that is, the voltage input from the first input end 501 of the comparator 500 is greater than the voltage input from the second input end 502 of the comparator 500, the comparator 500 outputs a comparison result of 1; or if the analog voltage $V_0$ is less than zero, that is, the voltage input from the first input end 501 of the comparator 500 is less than the voltage input from the second input end 502 of the comparator 500, the comparator 500 outputs a comparison result of 0, and the comparison result may correspond to the highest bit $B_{N-1}$ of the N-bit binary code.

Further, the SAR logic circuit 600 may determine the highest bit of the N-bit binary code according to the comparison result, and then control voltages connected to a corresponding first switch and second switch according to the highest bit. For example, if the highest bit is 1, the SAR logic circuit 600 may control the first switch $K_{1N}$ to be connected to VDD and the second switch $K_{2N}$ to be connected to GND so that the first resistor $R_{1N}$ is connected to VDD, and the second resistor $R_{2N}$ is connected to GND; or if the highest bit is 0, the SAR logic circuit may control the first switch $K_{1N}$ to be connected to GND and the second switch $K_{2N}$ to be connected to VDD so that the first resistor $R_{1N}$ is connected to GND, and the second resistor $R_{2N}$ is connected to VDD.

In a second stage, the DAC outputs a next analog current $I_1$ according to the connections of the first switch and the second switch to VDD or GND, where a difference between the analog current $I_1$ and the analog current Jo is an amperage distributed when the first resistor $R_{1N}$ and the second resistor $R_{2N}$ are connected to VDD or GND. Further, the differential TIA 30 may calculate a difference between the analog current $I_1$ and the interference current $I_{bg}$, and output an analog voltage $V_1$. The comparator 500 determines a next comparison result according to the analog voltage $V_1$, and the comparison result corresponds to a second most significant bit of the N-bit binary code. Then, the SAR logic circuit 600 may determine the second most significant bit of the N-bit binary code according to the comparison result, and may further control voltages connected to a corresponding first switch and second switch according to the second most significant bit.

The foregoing process is performed cyclically until each bit of the N-bit binary code is determined, and the corresponding first switches and second switches are controlled to be connected to corresponding voltages according to the N-bit binary code. In this case, an analog current $I_7$ output by the DAC 700 is equal to or approximately equal to the interference current $I_{bg}$. Therefore, according to the embodiment of the present application, the analog current output by the DAC could be successively approximate to the interference current through successive approximation logic, so as to achieve the effect of cancelling or approximately cancelling the interference current.

It should be understood that in the embodiment shown in FIG. 4, the successive approximation is started only with an initial state of 0000000, and in other alternative embodiments, the successive approximation may be started with other states. For example, the successive approximation is started with an initial state of 1111111, and in this way, only the logic implementation of the SAR logic circuit needs to be adjusted. That is, in the initial state, the N switches may be connected to any voltage. The specific principles are similar, which will not be repeated redundantly herein.

It should be noted that the embodiment of the present application is described only by an example that the first voltage is VDD and the second voltage is the ground voltage, which should not constitute any limitation to the embodiment of the present application. In the embodiment of the present application, the first voltage and the second voltage may be any level or any voltage. When the first voltage and the second voltage are a combination of other voltages, only the control logic of the SAR logic circuit needs to be adjusted. The implementation principles are similar, which will not be repeated redundantly herein.

It can be understood that the use of the single-ended resistive DAC shown in FIG. 3 is beneficial for reducing the number of resistors used, thereby simplifying the circuit structure. Compared with the use of the resistive DAC shown in FIG. 3, the resistive DAC shown in FIG. 4 uses resistor arrays with differential structures, which improves accuracy of the SAR ADC accordingly.

It should be understood that in the embodiment of the present application, the current cancellation circuit may further include a clock circuit configured to generate a periodic clock signal, the SAR logic circuit is configured to output a generated binary code to the DAC based on the control of the clock signal, and the comparator may perform comparison on the analog voltage and the like based on the control of the clock signal.

It should also be understood that in interference light cancellation, in some embodiments, the interference light signal may also be converted in a voltage signal. In this case, the current cancellation circuit in the embodiment of the present application may be configured for voltage cancellation, the DAC may adopt a voltage output type DAC, such as a capacitive DAC. The analog voltage output by the DAC is controlled by the SAR logic circuit to be successively approximate to the voltage signal generated from the interference light signal, thereby achieving the purpose of cancelling the interference light. The implementation principles are similar, which will not be repeated redundantly herein.

It should be understood that in some embodiments, the current cancellation circuit may also include the photoelectric sensor described above. That is, the photoelectric sensor may belong to the current cancellation circuit.

Figure 5:
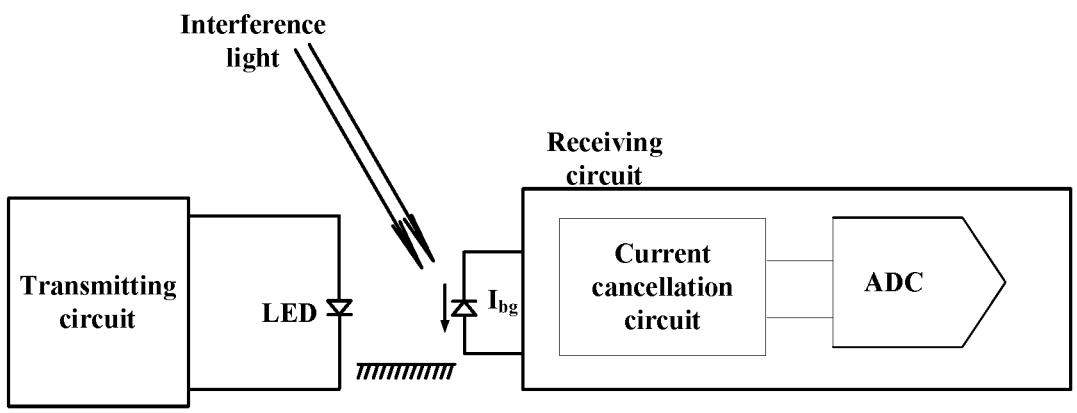
FIG. 5 is a schematic diagram of one application scenario of a current cancellation circuit according to an embodiment of the present application.

FIG. 5 is a schematic diagram of one application scenario of a current cancellation circuit according to an embodiment of the present application. Specifically, the current cancellation circuit may be applied to various related applications based on infrared detection technologies, such as heart rate detection based on PPG.

In an example of a heart rate detection device based on the PPG technology, the heart rate detection device may include a transmitting circuit and a receiving circuit, where the transmitting circuit may be configured to transmit infrared light, for example, to transmit infrared light through a light emitting diode (LED). Further, the infrared light signal is received through a photoelectric sensor of the receiving circuit, such as a photodiode, the infrared light signal is photoelectrically converted into an electric signal, and then transmitted to the subsequent receiving circuit for processing to determine an intensity of reflected light after absorption by human blood and tissues, thereby determining a heart rate of a human.

In the embodiment of the present application, the photoelectric sensor is connected to an input end of a current-voltage conversion circuit in the current cancellation circuit, and configured to receive the infrared light signal and perform photoelectric conversion on the received infrared light signal to obtain a current signal; the current signal is input to the input end of the current-voltage conversion circuit; and the receiving circuit further includes an ADC, where the ADC is connected to an output end of the current-voltage conversion circuit, and configured to receive an analog voltage output by the current-voltage conversion circuit and perform analog-to-digital conversion on the analog voltage to determine heart rate information of the human.

Optionally, in the embodiment of the present application, performing the heart rate detection mainly includes two processes:

in a first stage, interference light detection is mainly performed. That is, the magnitude of an interference current caused by an interference light signal is determined by the current cancellation circuit. In this stage, the transmitting circuit does not transmit a light signal, a light signal received by the photoelectric sensor is mainly the interference light signal, and a current obtained based on conversion of the interference light signal is mainly the interference current. The current cancellation circuit of the embodiment of the present application is sampled, successive approximation is performed based on the interference current, and a digital signal output by an SAR ADC in the current cancellation circuit may be determined. Further, a DAC in the current cancellation circuit may be controlled to output a corresponding analog current through the digital signal, and the analog current is equal to or approximately equal to the interference current. Reference is made to the relevant description of the foregoing embodiments for the specific implementation, which will not be repeated redundantly herein.

Since the analog current is equal to or approximately equal to the interference current, the current-voltage conversion circuit calculates a difference between the two, the output analog voltage is approximately zero, and further the output of the ADC is also approximately zero.

In a second stage, that is, a heart rate monitoring stage, in this stage, the transmitting circuit transmits a light signal for heart rate detection, and the light signal received by the photoelectric sensor includes both the interference light signal and the infrared light signal for heart rate monitoring. In this way, a current output by the photoelectric sensor is a mixed current including the interference current and a signal current generated from the infrared light signal. Meanwhile, the DAC still outputs the analog current, and the current-voltage conversion circuit receives the mixed current and the analog current, and calculates a difference between the mixed current and the analog current. A difference current obtained at this time is basically a signal current, and the analog voltage output to the ADC is basically generated from the signal current. That is, the analog voltage output by the current-voltage conversion circuit is basically a useful signal. Further, accuracy of the heart rate detection could be improved by performing heart rate monitoring based on the analog voltage.

An embodiment of the present application further provides a wearable device, and the wearable device may include the current cancellation circuit. Optionally, the wearable device may further include a photoelectric sensor, the ADC described above, or the like. The current cancellation circuit may be the current cancellation circuit described in the foregoing embodiments, and the ADC may be the ADC described above. The current cancellation circuit may be configured to cancel an interference current obtained by photoelectric conversion of an interference light signal by the photoelectric sensor so that signals received by the ADC are all useful signals, thereby improving accuracy of PPG detection. Reference is made to the relevant description of the foregoing embodiments for the specific implementation, which will not be repeated redundantly herein.

It should be understood that the wearable device in the embodiment of the present application may be a wristband, a headset, or the like, and the wearable device may be configured to implement functions such as heart rate detection and exercise step recording.

In the embodiments provided in the present application, it should be understood that the disclosed device may be implemented in other manners. For example, the device embodiments described above are merely exemplary, e.g., the division of the units is merely a logic function division, and other division manners may exist in practical implementation. For example, a plurality of units or components may be combined or integrated to another system.

Described above is merely the specific embodiments of the present application, whereas the protection scope of the present application is not limited to this. Any person who is skilled in and familiar with the present technical field may readily conceive of changes or substitutions within the technical scope disclosed in the present application, and all of these shall fall within the protection scope of the present application. Therefore, the protection scope of the present application shall be subject to the protection scope of the claims.

What is claimed is:

1. A current cancellation circuit, comprising:
a current-voltage conversion circuit and a successive approximation (SAR) analog-to-digital converter (ADC), wherein the SAR ADC comprises a digital-to-analog converter (DAC), an SAR logic circuit and a comparator, wherein an output end of the DAC is connected to an input end of the current-voltage conversion circuit, the input end of the current-voltage conversion circuit is simultaneously connected to an output end of a photoelectric sensor, output ends of the current-voltage conversion circuit are connected to input ends of the comparator, an output end of the comparator is connected to an input end of the SAR logic circuit, and an output end of the SAR logic circuit is connected to an input end of the DAC;
wherein in a first stage:
the current-voltage conversion circuit is configured to receive an analog current output by the DAC and an interference current output by the photoelectric sensor, calculate a difference between the analog current and the interference current, and output an analog voltage, wherein the interference current is obtained by photoelectric conversion of an interference light signal by the photoelectric sensor;
the comparator is configured to receive the analog voltage output by the current-voltage conversion circuit, and output a comparison result according to the analog voltage; and
the DAC is configured to output the analog current according to a digital signal corresponding to the comparison result that is output by the SAR logic circuit, and the analog current is used to cancel the interference current output by the photoelectric sensor;
wherein in a second stage:
the current-voltage conversion circuit is further configured to calculate a difference between a mixed current output by the photoelectric sensor and the analog current output by the DAC in the first stage, wherein the mixed current output comprises the interference current and a signal current generated from a light signal for heart rate monitoring.

2. The current cancellation circuit according to claim 1, wherein the SAR logic circuit is configured to:
determine the digital signal, and control, according to the digital signal, the DAC to output a next analog current so that the next analog current is more approximate to the interference current.

3. The current cancellation circuit according to claim 2, wherein the DAC is a resistive DAC, the resistive DAC comprises N first resistors, the current cancellation circuit further comprises N first switches, and the N first resistors are in one-to-one correspondence to the N first switches, wherein N is a number of bits of the digital signal output by the SAR ADC; and
the SAR logic circuit is further configured to:
control, according to the digital signal, a corresponding first switch so that a first resistor corresponding to the first switch is connected to a first voltage or a second voltage.

4. The current cancellation circuit according to claim 3, wherein the DAC is a single-ended resistive DAC, and the current-voltage conversion circuit is a transimpedance amplifier (TIA), wherein the TIA comprises a first input end, a common mode input end, a first output end and a second output end, an output end of the single-ended resistive DAC is connected to the first input end of the TIA, an output end of the photoelectric sensor is also connected to the first input end of the TIA, the common mode input end of the TIA is configured to input a common mode voltage, the first output end of the TIA is connected to a first input end of the comparator, the second output end of the TIA is connected to a second input end of the comparator, an output end of the comparator is connected to an input end of the SAR logic circuit, and an output end of the SAR logic circuit is connected to an input end of the single-ended resistive DAC.

5. The current cancellation circuit according to claim 3, wherein the DAC is a differential resistive DAC, the differential resistive DAC further comprises N second resistors, the current cancellation circuit further comprises N second switches, the N second resistors are in one-to-one correspondence to the N second switches, and the SAR logic circuit is further configured to:

control, according to an inverted signal of the digital signal, a corresponding second switch so that a second resistor corresponding to the second switch is connected to the second voltage or the first voltage.

6. The current cancellation circuit according to claim 5, wherein the SAR logic circuit is configured to:

control, if the digital signal is 1, the second switch so that the second resistor corresponding to the second switch is connected to the second voltage; or control, if the digital signal is 0, the second switch so that the second resistor corresponding to the second switch is connected to the first voltage.

7. The current cancellation circuit according to claim 5, wherein the current-voltage conversion circuit is a differential TIA, the differential TIA comprises a first input end, a second input end, a common mode input end, a first output end and a second output end, a first output end and a second output end of the differential resistive DAC are respectively connected to the first input end and the second input end of the differential TIA, a first end and a second end of the photoelectric sensor are respectively connected to the first input end and the second input end of the differential TIA, the common mode input end of the differential TIA is configured to input a common mode voltage, the first output end and the second output end of the differential TIA are respectively connected to a first input end and a second input end of the comparator, an output end of the comparator is connected to an input end of the SAR logic circuit, and an output end of the SAR logic circuit is connected to an input end of the differential resistive DAC.

8. The current cancellation circuit according to claim 3, wherein the first voltage is a reference voltage, and the second voltage is a ground voltage or a common mode voltage.

9. The current cancellation circuit according to claim 1, wherein the SAR logic circuit determines the digital signal according to a dichotomy.

10. The current cancellation circuit according to claim 1, wherein the DAC is configured to:

output, according to a current analog current and the digital signal, a next analog current, and input the next analog current to the current-voltage conversion circuit.

11. The current cancellation circuit according to claim 1, wherein the DAC is a resistive DAC, the resistive DAC comprises N first resistors, the current cancellation circuit further comprises N first switches, and the N first resistors are in one-to-one correspondence to the N first switches, wherein N is a number of bits of the digital signal output by the SAR ADC; and the SAR logic circuit is further configured to:

control, according to the digital signal, a corresponding first switch so that a first resistor corresponding to the first switch is connected to a first voltage or a second voltage.

12. The current cancellation circuit according to claim 11, wherein the SAR logic circuit is configured to:

control, if the digital signal is 1, the first switch so that the first resistor corresponding to the first switch is connected to the first voltage; or control, if the digital signal is 0, the first switch so that the first resistor corresponding to the first switch is connected to the second voltage.

13. The current cancellation circuit according to claim 12, wherein the DAC is a single-ended resistive DAC, and the current-voltage conversion circuit is a transimpedance amplifier (TIA), wherein the TIA comprises a first input end, a common mode input end, a first output end and a second output end, an output end of the single-ended resistive DAC is connected to the first input end of the TIA, an output end of the photoelectric sensor is also connected to the first input end of the TIA, the common mode input end of the TIA is configured to input a common mode voltage, the first output end of the TIA is connected to a first input end of the comparator, the second output end of the TIA is connected to a second input end of the comparator, an output end of the comparator is connected to an input end of the SAR logic circuit, and an output end of the SAR logic circuit is connected to an input end of the single-ended resistive DAC.

14. The current cancellation circuit according to claim 12, wherein the DAC is a differential resistive DAC, the differential resistive DAC further comprises N second resistors, the current cancellation circuit further comprises N second switches, the N second resistors are in one-to-one correspondence to the N second switches, and the SAR logic circuit is further configured to:

control, according to an inverted signal of the digital signal, a corresponding second switch so that a second resistor corresponding to the second switch is connected to the second voltage or the first voltage.

15. The current cancellation circuit according to claim 1, wherein the photoelectric sensor is a photodiode.

16. A heart rate detection device, comprising:

a photoelectric sensor;

a current cancellation circuit, the current cancellation circuit comprises:

a current-voltage conversion circuit and a successive approximation (SAR) analog-to-digital converter (ADC), wherein the SAR ADC comprises a digital-to-analog converter (DAC), an SAR logic circuit and a comparator, wherein an output end of the DAC is connected to an input end of the current-voltage conversion circuit, the input end of the current-voltage conversion circuit is simultaneously connected to an output end of the photoelectric sensor, output ends of the current-voltage conversion circuit are connected to input ends of the comparator, an output end of the comparator is connected to an input end of the SAR logic circuit, and an output end of the SAR logic circuit is connected to an input end of the DAC;

wherein in a first stage:

the current-voltage conversion circuit is configured to receive an analog current output by the DAC and an interference current output by the photoelectric sensor, calculate a difference between the analog current and the interference current, and output an analog voltage, wherein the interference current is obtained by photoelectric conversion of an interference light signal by the photoelectric sensor;

the comparator is configured to receive the analog voltage output by the current-voltage conversion circuit, and output a comparison result according to the analog voltage; and the DAC is configured to output the analog current according to a digital signal corresponding to the comparison result that is output by the SAR logic circuit, and the analog current is used to cancel the interference current output by the photoelectric sensor;

wherein in a second stage:

the current-voltage conversion circuit is further configured to calculate a difference between a mixed current output by the photoelectric sensor and the analog current output by the DAC in the first stage, wherein the mixed current output comprises the interference current and a signal current generated from a light signal for heart rate monitoring.

17. The heart rate detection device according to claim 16, wherein the heart rate detection device further comprises:

a transmitting circuit configured to transmit a light signal for heart rate detection; and a receiving circuit comprising the photoelectric sensor and an analog-to-digital converter (ADC);

wherein the photoelectric sensor is connected to the input end of the current-voltage conversion circuit in the current cancellation circuit, and configured to receive the light signal for heart rate monitoring, and perform photoelectric conversion on the received light signal to obtain a current signal, and input the current signal to the input end of the current-voltage conversion circuit; and the ADC is connected to an output end of the current-voltage conversion circuit, and configured to receive an analog voltage output by the current-voltage conversion circuit.

18. The heart rate detection device according to claim 17, wherein in the first stage, the transmitting circuit does not transmit a light signal, the photoelectric sensor receives the interference light signal and performs photoelectric conversion on the interference light signal to obtain the interference current; and in the second stage, the transmitting circuit transmits the light signal for heart rate detection, the photoelectric sensor receives the interference light signal and the light signal for heart rate monitoring, and performs photoelectric conversion on the interference light signal and the light signal for heart rate monitoring to obtain the mixed current.

19. A wearable device, comprising: the heart rate detection device according to claim 16.

* * * * *